US006780599B2

(12) United States Patent
Hamilton et al.

(10) Patent No.: US 6,780,599 B2
(45) Date of Patent: Aug. 24, 2004

(54) METHODS OF DETECTING INTERACTIONS BETWEEN PROTEINS, PEPTIDES OR LIBRARIES THEREOF USING FUSION PROTEINS

(75) Inventors: Andrew D. Hamilton, Guilford, CT (US); Indraneel Ghosh, Tucson, AZ (US); Lynne Regan, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/853,897

(22) Filed: May 14, 2001

(65) Prior Publication Data

US 2002/0146701 A1 Oct. 10, 2002

Related U.S. Application Data

(60) Provisional application No. 60/203,712, filed on May 12, 2000.

(51) Int. Cl.[7] .............................................. G01N 33/53
(52) U.S. Cl. ............................ 435/7.1; 435/7.8; 435/6; 435/5; 435/194; 435/320.1; 435/69.1; 530/350; 536/23.4
(58) Field of Search ........................ 530/350; 435/7.1, 435/5, 6, 194, 320.1, 7.8, 69.1; 536/23.4

(56) References Cited

U.S. PATENT DOCUMENTS

| | | | |
|---|---|---|---|
| 6,180,343 B1 | 1/2001 | Anderson et al. | |
| 6,200,762 B1 | 3/2001 | Zlokarnik et al. | |
| 6,270,964 B1 | 8/2001 | Michnick et al. | |
| 6,428,951 B1 | 8/2002 | Michnick et al. | |
| 2002/0037999 A1 * | 3/2002 | Mayer | 530/350 |

FOREIGN PATENT DOCUMENTS

| | | |
|---|---|---|
| WO | WO 98/34120 | 8/1998 |
| WO | WO 98/34120 A1 | 8/1998 |
| WO | WO 01/00866 | 1/2001 |
| WO | WO 01/87919 A2 | 11/2001 |

OTHER PUBLICATIONS

Azevedo, J, et al.; "Characterization of a . . . " Arch Virol 2001; 146(1):51–7.
Katz, Bz et al.; "Green fluorescent . . . " Biotechniques 1998 Aug.; 25(2):298–302, 304.
Hodges, RS; "Boehringer Mannheim award . . . " Biochem Cell Biol 1996; 74(2):133–54.
Gernert, KM et al.; "The Alacoil:a very tight , . . . " Proyein Sci 1995 Nov.; 4(11):2252–60.
Dutch, Re et al.; "Paramyxovirus fusion protein: . . . " Virology Feb. 1, 1999;254 (1) :147–59.
Ghosh, I. et al.; "Antiparallel Leucine Zipper . . . " Dept. of Chem. and Dept. of Mol. Biophysics and BioChem. Yale Univ. pp 1–3.
Geoffrey S. Baird et al., Proc. Natl. Acad. Sci. USA, vol. 96, pp. 11241–11246, Sep. 1999.
Stephen W. Michnick, Current Opinion in Structural Biology 2001, vol. 11, pp. 472–477.
Jie Chen et al., Proc. Natl. Acad. Sci. USA, vol. 92, pp. 4947–4951, May 1995.
Indraneel Ghosh et al., J. Am. Chem. Soc. 2000, vol. 122, pp. 5658–5659.
Chang–Deng Hu et al., Molecular Cell, vol. 9, pp. 789–798, Apr. 2002.
Takeharu Nagai et al., PNAS, Mar. 13, 2001, vol. No. 6, pp. 3197–3202.
Takeharu Nagai et al., Nature Biotechnology, vol. 20, Jan. 2002, pp. 87–90.
Junichi Nakai et al., Nature Biotechnology, vol. 19, Feb. 2001, pp. 137–141.
Nils Johnsson et al., Proc. Natl. Acad. Sci. USA, vol. 91, pp. 10340–10344, Oct. 1994.
Ingrid Remy et al., PNAS, vol. 98, No. 4, Jul. 3, 2001, pp. 7678–7683.
Fabio Rossi et al., Proc. Natl. Acad. Sci. USA, vol. 94, pp. 8405–8410, Aug. 1997.
Simon Topell et al., FEBS Letters, vol. 457, 1999, pp. 283–289.
Henrik Ostergaard et al., The EMBO Journal, vol. 20, No. 21, pp. 5853–5862, 2001.
Ghosh, Am. Chem. Soc. 2000, Ghosh ja994421w.
Majid R. Abedi et al., Nucleic Acids Research, 1998. vol. 26, No. 2, pp. 623–630.
Siegfried Alberti et al., The EMBO Journal, vol. 12, No. 8, pp. 3227–3236, 1993.
Erin K. O'Shea et al., "Peptide 'Velcro*': design of a heterodimeric coiled coil", Current Biology, 1993, vol. 3, No. 10, pp. 658–667.

* cited by examiner

*Primary Examiner*—T. D. Wessendorf
(74) *Attorney, Agent, or Firm*—Birch, Stesart, Kolasch & Birch, LLP

(57) ABSTRACT

The present invention provides assays using fusion proteins with GFP fragments and test polypeptides for investigating protein-protein interactions.

5 Claims, 6 Drawing Sheets

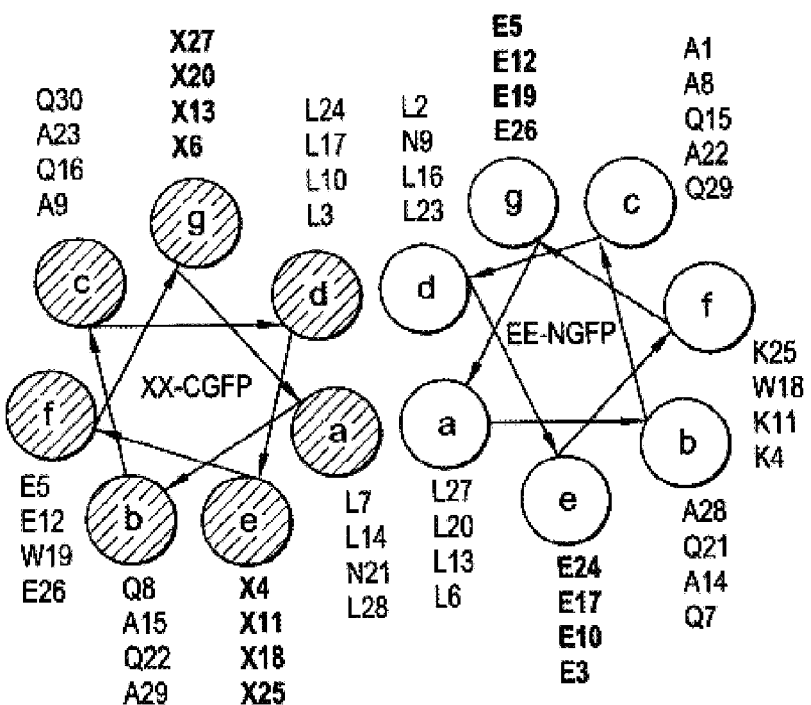
FIG.5a
FIG.5b
Residue selected at randomized positions
| 4 | 6 | 11 | 13 | 18 | 20 | 25 | 27 |
|---|---|----|----|----|----|----|----|
| K | K | E  | K  | K  | K  | K  | K  |
| K | K | K  | K  | E  | K  | K  | K  |
| K | K | K  | K  | E  | K  | K  | K  |
| K | K | K  | K  | K  | K  | E  | K  |
| E | K | K  | E  | K  | K  | K  | K  |
| E | K | K  | K  | K  | E  | K  | K  |
| K | E | K  | K  | K  | E  | K  | K  |
| K | E | K  | K  | K  | K  | E  | K  |
| K | K | E  | K  | K  | E  | K  | K  |
| K | K | E  | K  | K  | K  | E  | K  |
| K | K | K  | K  | E  | K  | E  | K  |
| K | K | K  | K  | E  | K  | E  | K  |
| E | K | E  | K  | K  | E  | K  | K  |
| E | K | E  | K  | K  | E  | K  | K  |
| E | K | E  | K  | K  | E  | K  | E  |
| K | K | E  | K  | E  | K  | K  | E  |
FIG.5c

```
SEQUENCE LISTING

<160> NUMBER OF SEQ ID NOS: 9

<210> SEQ ID NO 1
<211> LENGTH: 29
<212> TYPE: PRT
<213> ORGANISM: Artificial Sequence
<220> FEATURE:
<223> OTHER INFORMATION: Designed leucine zipper (NZ)

<400> SEQUENCE: 1

Ala Leu Lys Lys Glu Leu Gln Ala Asn Lys Lys Glu Leu Ala Gln Leu
1               5                   10                  15

Lys Trp Glu Leu Gln Ala Leu Lys Lys Glu Leu Ala Gln
            20                  25

<210> SEQ ID NO 2
<211> LENGTH: 30
<212> TYPE: PRT
<213> ORGANISM: Artificial Sequence
<220> FEATURE:
<223> OTHER INFORMATION: Designed leucine zipper (CZ)

<400> SEQUENCE: 2

Glu Gln Leu Glu Lys Lys Leu Gln Ala Leu Glu Lys Lys Leu Ala Gln
1               5                   10                  15

Leu Glu Trp Lys Asn Gln Ala Leu Glu Lys Lys Leu Ala Gln
            20                  25                  30

<210> SEQ ID NO 3
<211> LENGTH: 162
<212> TYPE: PRT
<213> ORGANISM: Artificial Sequence
<220> FEATURE:
<223> OTHER INFORMATION: Synthetic peptide sequence NGFP

<400> SEQUENCE: 3

Met Ala Ser Lys Gly Glu Glu Leu Phe Thr Gly Val Val Pro Leu Leu
1               5                   10                  15

Val Glu Leu Asp Gly Asp Val Asn Gly His Lys Phe Ser Val Ser Gly
            20                  25                  30
```

-continued

```
Glu Gly Gly Asp Ala Thr Tyr Gly Lys Leu Thr Leu Lys Phe Ile Cys
            35                  40                  45

Thr Thr Gly Lys Leu Pro Val Pro Trp Pro Leu Thr Val Thr Thr Leu
 50                  55                  60

Cys Tyr Gly Val Gln Cys Phe Ser Arg Tyr Pro Asp His Met Lys Arg
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
130                 135                 140

Tyr Asn His Asn Val Leu Ile Met Ala Asp Lys Gln Gly Gly Ser Gly
145                 150                 155                 160

Ser Gly
```

```
<210> SEQ ID NO 4
<211> LENGTH: 192
<212> TYPE: PRT
<213> ORGANISM: Artificial Sequence
<220> FEATURE:
<223> OTHER INFORMATION: Synthetic peptide sequence NZGFP

<400> SEQUENCE: 4
```

```
Met Ala Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
 50                  55                  60

Leu Cys Tyr Gly Val Gln Cys Phe Ser Arg Tyr Pro Asp His Met Lys
 65                  70                  75                  80

Arg His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
130                 135                 140

Asn Tyr Asn His Asn Val Leu Ile Met Ala Asp Lys Gln Gly Gly Ser
145                 150                 155                 160

Gly Ser Gly Ala Leu Lys Lys Glu Leu Gln Ala Asn Lys Lys Glu Leu
                165                 170                 175

Ala Gln Leu Phe Trp Glu Leu Gln Ala Leu Lys Lys Glu Leu Ala Gln
            180                 185                 190
```

```
<210> SEQ ID NO 5
<211> LENGTH: 87
<212> TYPE: PRT
<213> ORGANISM: Artificial Sequence
<220> FEATURE:
<223> OTHER INFORMATION: Synthetic peptide sequence CGFP
```

```
<400> SEQUENCE: 5

Met Ala Ser Gly Gly Ser Gly Lys Asn Gly Ile Lys Val Asn Phe Lys
1               5                   10                  15

Thr His Asn Ile Glu Asp Gly Ser Val Gln Leu Ala Asp His Tyr Gln
            20                  25                  30

Gln Asn Thr Pro Ile Gly Asp Gly Pro Val Leu Leu Pro Asp Asn His
        35                  40                  45

Tyr Leu Ser Thr Gln Ser Ala Leu Ser Lys Asp Pro Asn Glu Lys Arg
    50                  55                  60

Asp His Met Val Leu Leu Glu Phe Val Thr Ala Ala Gly Ile Thr His
65                  70                  75                  80

Gly Met Asp Glu Leu Tyr Asn
                85

<210> SEQ ID NO 6
<211> LENGTH: 118
<212> TYPE: PRT
<213> ORGANISM: Artificial Sequence
<220> FEATURE:
<223> OTHER INFORMATION: Synthetic peptide sequence CZGFP

<400> SEQUENCE: 6

Met Ala Ser Glu Gln Leu Glu Lys Lys Leu Gln Ala Leu Glu Lys Lys
1               5                   10                  15

Leu Ala Gln Leu Glu Trp Lys Asn Gln Ala Leu Glu Lys Lys Leu Ala
            20                  25                  30

Gln Gly Gly Ser Gly Lys Asn Gly Ile Lys Val Asn Phe Lys Thr Arg
        35                  40                  45

His Asn Ile Glu Asp Gly Ser Val Gln Leu Ala Asp His Tyr Gln Gln
    50                  55                  60

Asn Thr Pro Ile Gly Asp Gly Pro Val Leu Leu Pro Asp Asn His Tyr
65                  70                  75                  80

Leu Ser Thr Gln Ser Ala Leu Ser Lys Asp Pro Asn Glu Lys Arg Asp
                85                  90                  95

His Met Val Leu Leu Glu Phe Val Thr Ala Ala Gly Ile Thr His Gly
            100                 105                 110

Met Asp Glu Leu Tyr Asn
        115

<210> SEQ ID NO 7
<211> LENGTH: 29
<212> TYPE: PRT
<213> ORGANISM: Artificial Sequence
<220> FEATURE:
<223> OTHER INFORMATION: Leucine zipper KK

<400> SEQUENCE: 7

Ala Gln Leu Lys Glu Lys Leu Gln Ala Leu Lys Glu Lys Leu Ala Gln
1               5                   10                  15

Lys Trp Lys Leu Asn Ala Leu Lys Glu Lys Leu Ala Gln
            20                  25

<210> SEQ ID NO 8
<211> LENGTH: 29
<212> TYPE: PRT
<213> ORGANISM: Artificial Sequence
<220> FEATURE:
<223> OTHER INFORMATION: Leucine zipper EE
```

```
<400> SEQUENCE: 8

Ala Leu Glu Lys Glu Leu Gln Ala Asn Glu Lys Glu Leu Ala Gln Leu
1               5                   10                  15

Glu Trp Glu Leu Gln Ala Leu Glu Lys Glu Leu Ala Gln
            20                  25

<210> SEQ ID NO 9
<211> LENGTH: 6
<212> TYPE: PRT
<213> ORGANISM: Artificial Sequence
<220> FEATURE:
<223> OTHER INFORMATION: Synthetic sequence used as an insert between
      adjacent residues at 10 internal insertion sites

<400> SEQUENCE: 9

Leu Glu Glu Phe Gly Ser
1               5
```

METHODS OF DETECTING INTERACTIONS BETWEEN PROTEINS, PEPTIDES OR LIBRARIES THEREOF USING FUSION PROTEINS

RELATED APPLICATIONS

This application claims the benefit of priority of U.S. Provisional Application 60/203,712, filed on May 12, 2000.

FIELD OF THE INVENTION

The present invention is related to the reassembly of fusion peptides into a functionally active protein complex. Specifically, the present invention provides a method of forming peptide complexes that associate through the combination of helical domains to form an antiparallel leucine zipper. The present invention is also related to the use of assays to investigate protein-protein interactions. The assays of the present invention involve the association of fusion proteins comprising GFP fragments and heterologous polypeptides into functionally active GFP that exhibits fluorescence.

BACKGROUND OF THE INVENTION

All publications and patent applications herein are incorporated by reference to the same extent as if each individual publication or patent application was specifically and individually indicated to be incorporated by reference.

Green Fluorescent Protein

Green fluorescent protein (GFP), a relatively small protein comprising 238 amino acids, is the ultimate source of fluorescent light emission in the jellyfish *Aequorea victoria*. The gene for GFP was first cloned by Prasher et al. (1992, Gene, 111:229–233), and cDNA for the protein produces a fluorescent product identical to that of native protein when expressed in prokaryotic (*E. coli*) and eucaryotic (*C. elegans*) cells (Chalfie et al., 1994, Science, 263, 802–805).

The GFP excitation spectrum shows an absorption band (blue light) maximally at 395 nm with a minor peak at 470 nm, and an emission peak (green light) at 509 nm. The longer-wavelength excitation peak has greater photostability than the shorter peak, but is relatively low in amplitude (Chalfie et al., 1994, Science, 263: 802–805). The crystal structure of the protein and of several point mutants has been solved (Ormo et al., 1996, Science 273, 1392; Yang et al., Nature Biotechnol. 14, 1246). The fluorophore, consisting of a tripeptide at residues 65–67, is buried inside a relatively rigid beta-can structure, where it is almost completely protected from solvent access. The GFP absorption bands and emission peak arise from an internal p-hydroxybenzylideneimidazolidinone chromophore, which is generated by cyclization and oxidation of the tripeptide sequence Ser-Tyr-Gly sequence at residues 65–67 (Cody et al., 1993, Biochemistry 32: 1212–1218).

GFP fluorescence in procaryotic and eucaryotic cells does not require exogenous substrates and cofactors. Accordingly, GFP is considered to have tremendous potential in methods to monitor gene expression, cell development, or as an in situ tag for fusion proteins (Heim et al., 1994, P.N.A.S. USA, 91,12501–12504). Chalfie and Prasher, WO 95/07463 (Mar. 16, 1995), describe various uses of GFP, including a method of examining gene expression and protein localization in living cells. Methods are described wherein: 1) a DNA molecule is introduced into a cell, said DNA molecule having DNA sequence of a particular gene linked to DNA sequence encoding GFP such that the regulatory element of the gene will control expression of GFP; 2) the cell is cultured in conditions permitting the expression of the fused protein; and 3) detection of expression of GFP in the cell, thereby indicating the expression of the gene in the cell. Methods such as those described by Chalfie and Prasher are advantageous compared to previously reported methods which utilized β-galactosidase fusion proteins (Silhavy and Beckwith, 1985, Microbiol. Rev., 49, 398; Gould and Subramani, 1988, Anal. Biochem., 175, 5; Stewart and Williams, 1992, J. Gen. Microbiol., 138,1289) or luciferases, in that the need to fix cell preparations and/or add exogenous substrates and cofactors is eliminated.

GFP is a valuable marker for intracellular protein localization. However, the fusion of GFP with structural proteins can alter their properties, resulting in loss of fusion protein localization, decreased GFP fluorescence or both. The fluorescence of this protein is sensitive to a number of point mutations (Phillips, G. N., 1997, Curr. Opin. Struct. Biol. 7, 821–27). The fluorescence appears to be a sensitive indication of the preservation of the native structure of the protein, since any disruption of the structure allowing solvent access to the fluorophoric tripeptide will quench the fluorescence. Abedi et al. (1998, Nucleic Acids Res., 26, 623–30) have inserted peptides between residues contained in several GFP loops. Inserts of the short sequence LEEFGS (SEQ ID NO: 9) between adjacent residues at 10 internal insertion sites were tried. Of these, inserts at three sites, between residues 157–158, 172–173 and 194–195 gave fluorescence of at least 1% of that of wild type GFP. Only inserts between residues 157–158 and 172–173 had fluorescence of at least 10% of wild type GFP.

Protein Reassembly using Leucine Zipper

The unassisted reconstitution of proteins from peptide fragments has been demonstrated for several proteins; including ribonuclease (Richards et al., 1959, J. Biol. Chem. 234, 1459–1465), chymotrypsin inhibitor-2 (Gay et al., 1994, Biochemistry, 33, 7957–7963), tRNA synthetases (Shiba et al., 1992, Proc. Natl. Acad. Sci. U.S.A., 89, 1880–1884), and inteins (Southworth, et al., 1998, EMBO J., 17, 918–926). Protein reassembly has thus become an important avenue for understanding enzyme catalysis (Richards et al., 1959, J. Biol. Chem. 234, 1459–1465), protein folding (Gay et al., 1994, Biochemistry, 33, 7957–7963), and protein evolution (Shiba et al., 1992, Proc. Natl. Acad. Sci. U.S.A., 89, 1880–1884). Recently, assisted protein reassembly or "fragment complementation" has been applied to the in vivo detection of protein-protein interactions in such systems as dihydrofolate reductase (DHFR) (Pelletier et al., 1998, Proc. Natl. Acad. Sci. U.S.A., 95, 12141–12146; Remy et al., 1999, Proc. Natl. Acad. Sci. U.S.A., 96, 5394–5399; Pelletier et al., 1999, Nat. Biotechnol., 17, 683–690), ubiquitin (Karimova et al., 1998, Proc. Natl. Acad. Sci. U.S.A., 95, 5752–5756; Johnsson et al., 1994, Proc. Natl. Acad. Sci. U.S.A., 91, 10340–10344), and β-galactosidase (Rossi et al., 1997, Proc. Natl. Acad. Sci. U.S.A., 94, 8405–8410). These reassembly processes are contingent upon the proper choice of a dissection site within a protein and can be aided by techniques such as limited proteolysis, circular permutation (Baird et al., 1999, Proc. Natl. Acad. Sci. U.S.A., 96, 11241–11246; Topell et al., 1999, FEBS Lett., 457, 283–289; Zhang et al., 1993, Biochemistry, 32, 12311–12318; Regan, L., 1999, Curr. Opin. Struc. Biol., 9, 494–499) and loop insertions (Abedi et al., 1998, Nucleic Acid Res., 26, 623–630; Nobuhide et al., 1999, FEBS Lett., 453, 305–307).

The dissection and subsequent reassembly of a protein from peptidic fragments provide an avenue for controlling its tertiary structure and hence its function. Although a majority of leucine zippers associate in a parallel fashion, recent examples of both naturally occurring and designed antiparallel leucine zippers have appeared in the literature (Lupas, A., 1996, *Trends Biochem. Sc.* 21, 375–382; Kohn, W. D. et al., 1997, *S. J. Biol. Chem.* 272, 2583–2586; Bryson, J. W. et al., 1995, *Science*, 270, 935–941; Oakley M. G. et al., 1998, *Biochemistry*, 37, 12603–12610, Oakley, M. G. et al., 1997, *Biochemistry*, 36, 2544–2548). However, the prior art does not disclose the attachment of antiparallel leucine zippers to polypeptide fragments to form fusion proteins for reassembling the polypeptide fragments into functional proteins.

In contrast to parallel zippers, the antiparallel zippers are oriented in an opposite direction. Antiparallel Zippers have the advantage of occurring less frequently in natural proteins. Thus, antiparallel leucine zippers will interfere to a lesser extent with natural cellular proteins than parallel leucine zippers. Antiparallel attachment of leucine zippers to protein fragments (between a dissected peptide bond of the parent protein) requires a shorter amino acid linker region. As shown by the inventors of the present invention, as a preferred embodiment, a linker having 4–6 amino acids is sufficient (see Examples). Similar attachment of parallel leucine zippers would require >10 amino acids to span the necessary distance. The long unstructured linkers would be prone to proteolytic cleavage and be less stable in in vivo assays.

Katz et al. (1998, *Biotechniques*, 25, 298) describe a targeting approach based on noncovalent heterodimerization of GFP and cytoplasmic structural proteins using a leucine zipper designed to form high-affinity heterodimers. The complexes localized accurately to specific sites within cells, providing selective fluorescence labeling of subcellular structures such as microfilaments or focal contacts.

Protein-Protein Interaction Assays

The association and dissociation of proteins are crucial to all aspects of cell function. Examples of protein-protein interactions are evident in hormones and their respective receptors, in intracellular and extracellular signalling events mediated by proteins, in enzyme substrate interactions, in intracellular protein trafficking, in the formation of complex structures like ribosomes, viral coat proteins, and filaments, and in antigen-antibody interactions. Intracellular assays for detection of protein interactions and identification of their inhibitors have received wide attention with the completion of the human genome sequence.

U.S. Pat. No. 5,585,245 discloses a first fusion protein comprising an N-terminal subdomain of ubiquitin, fused to a non-ubiquitin protein or peptide and a second fusion protein comprising a C-terminal subdomain of ubiquitin, fused to the N-terminus of a non-ubiquitin protein or peptide. The patent discloses the use of these fusion proteins for studying protein-protein interactions. When contacted with one another, provided that the non-ubiquitin proteins or peptides interact (bind) with one another, the N- and C-terminal ubiquitin subdomains associate to reconstitute a quasi-native ubiquitin moiety which is recognized and cleaved by ubiquitin-specific proteases. However, this assay requires the use of additional cellular factors, such as the ubiquitin-specific proteases, for detection of protein-protein interaction. Thus, this assay is not feasible for high throughput screening of cDNA libraries.

U.S. Pat. No. 5,362,625 discloses omega-acceptor and omega-donor polypeptides (comprising about two-thirds and one-third of the β-galactosidase molecule amino and carboxyl termini, respectively), prepared by recombinant DNA techniques, DNA synthesis, or chemical polypeptide synthesis techniques, which are capable of interacting to form an active enzyme complex having catalytic activity characteristic of β-galactosidase. The patent also describes the use of these polypeptides in enzyme complementation assays for qualitative and quantitative determination of a suspected analyte in a sample.

The yeast two-hybrid system for detecting protein-protein interactions in Saccharomyces cerevisiae (Fields and Song, 1989, *Nature*, 340:245–246; U.S. Pat. No. 5,283,173 by Fields and Song) is well known in the art. This assay utilizes the reconstitution of a transcriptional activator like GAL4 (Johnston, 1987, *Microbiol. Rev.*, 51:458–476) through the interaction of two protein domains that have been fused to the two functional units of the transcriptional activator: the DNA-binding domain and the activation domain. This is possible due to the bipartite nature of certain transcription factors like GAL4. Being characterized as bipartite signifies that the DNA-binding and activation functions reside in separate domains and can function in trans (Keegan et al., 1986, *Science* 231:699–704). The reconstitution of the transcriptional activator is monitored by the activation of a reporter gene like the lacZ gene that is under the influence of a promoter that contains a binding site (Upstream Activating Sequence or UAS) for the DNA-binding domain of the transcriptional activator. This method is most commonly used either to detect an interaction between two known proteins (Fields and Song, 1989, *Nature*, 340:245–246) or to identify interacting proteins from a population that would bind to a known protein (Durfee et al., 1993, *Genes Dev.*, 7:555–569; Gyuris et al., 1993, *Cell*, 75:791–803; Harper et al., 1993, *Cell*, 75:805–816; Vojtek et al., 1993, *Cell*, 74:205–214). Like the ubiquitin system, additional factors are required for detection of the protein-protein interaction. Additionally, in the yeast two-hybrid system, the protein interaction must occur in the nucleus of the yeast.

WO 98/34120 describes protein fragment complementation assays for detecting bimolecular interactions. The assays comprise coexpression of fusion peptides consisting of N- and C-terminal fragments of murine DHFR fused to GCN4 leucine zipper sequences in *E. coli* to form colony. Colony formation only occurs when both DHFR fragments are present and contain leucine-zipper forming sequences. The published patent application contemplates the use of the assay to study molecular interactions including protein-protein, protein-DNA, protein-RNA, protein-carbohydrate, and protein-small molecule interactions, and for screening cDNA libraries for binding of a target protein with unknown proteins or libraries of small organic molecules for biological activity. WO 98/34120 also contemplates the use of GFP in the protein fragment complementation assay. However, the published patent application does not suggest fusing antiparallel leucine zipper to DHFR or GFP for reconstitution. GCN4 disclosed in the published application and routinely used by skilled artisan to reassemble proteins especially in the yeast two hybrid system, is a parallel zipper. Antiparallel and parallel zippers orient proteins in opposite direction; thus, it is not predictable that an antiparallel zipper can be substituted for a parallel zipper.

Additionally, all protein reassembly strategies disclosed in WO 98/34120 are for reassembly of multi domain proteins such as DHFR. The two dissected domains of DHFR can fold separately and only need to be brought into close proximity by attached proteins. There is no precedent for rational dissection of a single domain protein such as GFP that can be accomplished based upon the WO 98/34120. WO 98/34120 does not teach how to rationally dissect single domain proteins that can be subsequently reassembled. Finally, the ability to identify and characterize appropriate sites for dissecting a single domain protein is not validated or demonstrated in WO 98/34120.

U.S. Pat. No. 6,180,343 relates to the use of fluorescent proteins, particularly green fluorescent protein (GFP), in fusion constructs with random and defined peptides and peptide libraries, to increase the cellular expression levels, decrease the cellular catabolism, increase the conformational stability relative to linear peptides, and to increase the steady state concentrations of the random peptides and random peptide library members expressed in cells for the purpose of detecting the presence of the peptides and screening random peptide libraries. The patent does not contemplate the use of antiparallel leucine zipper for reconstituting GFP nor the use of peptides that associate with each other to reconstitute GFP and to provide a detection signal.

SUMMARY OF THE INVENTION

The present invention provides protein complexes comprising a first and second peptide, each of said peptides being joined, operably linked, or fused to a heterologous helical domain, said helical domains being noncovalently associated to form an antiparallel leucine zipper. The peptides of the protein complexes form a functional signaling moiety such as a reporter, a marker, or a biosensor upon non-covalent association of the helical domains into an antiparallel leucine zipper. In one embodiment, each of the peptides is joined to a helical domain via a linker. In a preferred embodiment, each of the helical domains comprises an amino acid sequence as set forth in SEQ ID NO: 1 or SEQ ID NO: 2. Preferably, each of the first and second peptides comprises a distinct portion of green fluorescent protein (GFP).

In one aspect, the present invention provides fusion proteins comprising a peptide and a helical domain, said helical domain forming an antiparallel leucine zipper when it noncovalently associates with a complementary helical domain. The helical domain is a heterologous or distinct protein or polypeptide fragment, relative to the peptide of the fusion protein. The fusion protein may further comprise a linker moiety interposed between the peptide and the helical domain. In a preferred embodiment, the peptide comprises a peptide derived from green fluorescent protein (GFP).

In another aspect, the present invention provides nucleic acids encoding fusion proteins comprising a peptide and helical domain, said helical domain forming an antiparallel leucine zipper when it noncovalently associates with a complementary helical domain.

The present invention provides a method of assembling a protein complex comprising (a) providing first and second helical domains that non-covalently associate to form an antiparallel leucine zipper; (b) providing first and second peptides; (c) producing fusion proteins by separately fusing said first helical domain to said first peptide and said second helical domain to said second peptide; and, (d) allowing the fusion proteins to form a protein complex mediated by the non-covalent association of the first and second helical domains into an antiparallel leucine zipper. The first and second peptides are distinct peptides. Preferably, they are distinct peptides derived from GFP, such that they comprise different GFP fragments.

In one embodiment of the disclosed method of assembling a protein complex, the protein complex comprises a signaling moiety and the helical domains comprise a leucine rich hydrophobic core. The helical domains may further comprise acidic residues and basic residues. The helical domains may further comprise a buried asparagine residue. The pair of helical domains preferably have the amino acid sequences as set forth in SEQ ID NO: 1 and SEQ ID NO: 2. In an alternative embodiment of the method, the step of producing the fusion proteins further comprises interposing a linker moiety between the peptide and the helical domain.

The present invention also provides a method of identifying a polypeptide that interacts with a known polypeptide comprising (a) producing a first fusion protein comprising the known polypeptide linked to a first GFP fragment; (b) producing a second fusion protein comprising a test polypeptide linked to a second GFP fragment, wherein association of the first and second GFP fragments results in a GFP that exhibits detectable fluorescence; (c) allowing the first fusion protein to associate with the second fusion protein to form a complex mediated by the non-covalent association of the known polypeptide and test polypeptide; and, (d) detecting whether, or to what extent, association of first and second GFP fragments occcurs, wherein association of GFP indicates that the test polypeptide interacts with the known polypeptide. Preferably, the first GFP peptide is NGFP and the second GFP peptide is CGFP.

In one aspect, the present invention provides a method of identifying a polypeptide that interacts with a known polypeptide comprising (a) producing a nucleic acid encoding a fusion protein comprising the known polypeptide linked to a first GFP fragment; (b) producing a plurality of nucleic acids encoding fusion proteins comprising a test polypeptide linked to a second GFP fragment, wherein association of the first and second GFP fragments results in a GFP that exhibits detectable fluorescence; (c) cotransforming or cotransfecting the nucleic acids of steps (a) and (b) into a host cell for expression of the encoded fusion proteins; (d) selecting colonies that exhibit fluorescence; and, (e) culturing the selected colonies to identify the test polypeptides that interact with the known polypeptide.

In a preferred embodiment of the constructs and methods of the present invention, the first GFP peptide is NGFP and the second GFP peptide is CGFP. Also, preferably, the nucleic acids of step (b) of the foregoing identification step are produced in the form of a combinatorial library.

In another aspect, the present invention provides a method of identifying a molecule that inhibits the activity of a known protein comprising (a) producing a first fusion protein comprising a first known polypeptide linked to a first GFP fragment; (b) producing a second fusion protein comprising a second polypeptide linked to a second GFP fragment, wherein the second polypeptide is known to interact with the first polypeptide and wherein association of the first and second GFP fragments results in a GFP that exhibits detectable fluorescence; (c) allowing the first fusion protein to associate with the second fusion protein to form a GFP complex mediated by the non-covalent association of the first and second polypeptide; (d) incubating a test molecule with the GFP complex; and, (e) detecting disassembly of the complex, wherein disassembly of the complex indicates that the test molecule inhibits the activity of the known protein. Preferably, the first GFP peptide is NGFP and the second GFP peptide is CGFP.

The present invention also contemplates a method of detecting protein-protein interactions comprising (a) producing a first fusion protein comprising a known polypeptide linked to a first GFP fragment; (b) producing a second fusion protein comprising a test polypeptide linked to a second GFP fragment, wherein association of the first and second GFP fragments results in a GFP that exhibits detectable fluorescence; (c) allowing the first fusion protein to associate with the second fusion protein to form a complex mediated by the non-covalent association of the known polypeptide and test polypeptide; and, (d) detecting reassembly of GFP, wherein reassembly of GFP indicates that the test polypeptide interacts with the known polypeptide.

A related method may further comprise obtaining nucleic acids encoding the first and second fusion proteins and cotransfecting or cotransforming the nucleic acids into a cell to obtain the first and second fusion protein.

BRIEF DESCRIPTION OF THE DRAWINGS

FIGS. 5A–C show fluorescence based selection. A. The "prey" leucine zipper attached to CGFP is randomized (X) at the e and g positions of the helix with either Lys (K) or Glu (E). and the "bait" leucine zipper attached to NGFP contains only Glu (E) residues at both e and g positions. B. SDS gel showing protein expression profiles of 10 cotransformed green fluorescent colonies from the selection. C. Tabulation of the residues selected in the library leucine zipper (XX-CGFP) by screening for fluorescence of cotransformed Escherichia coli cells.

DETAILED DESCRIPTION

1. General Description

Figure 1:
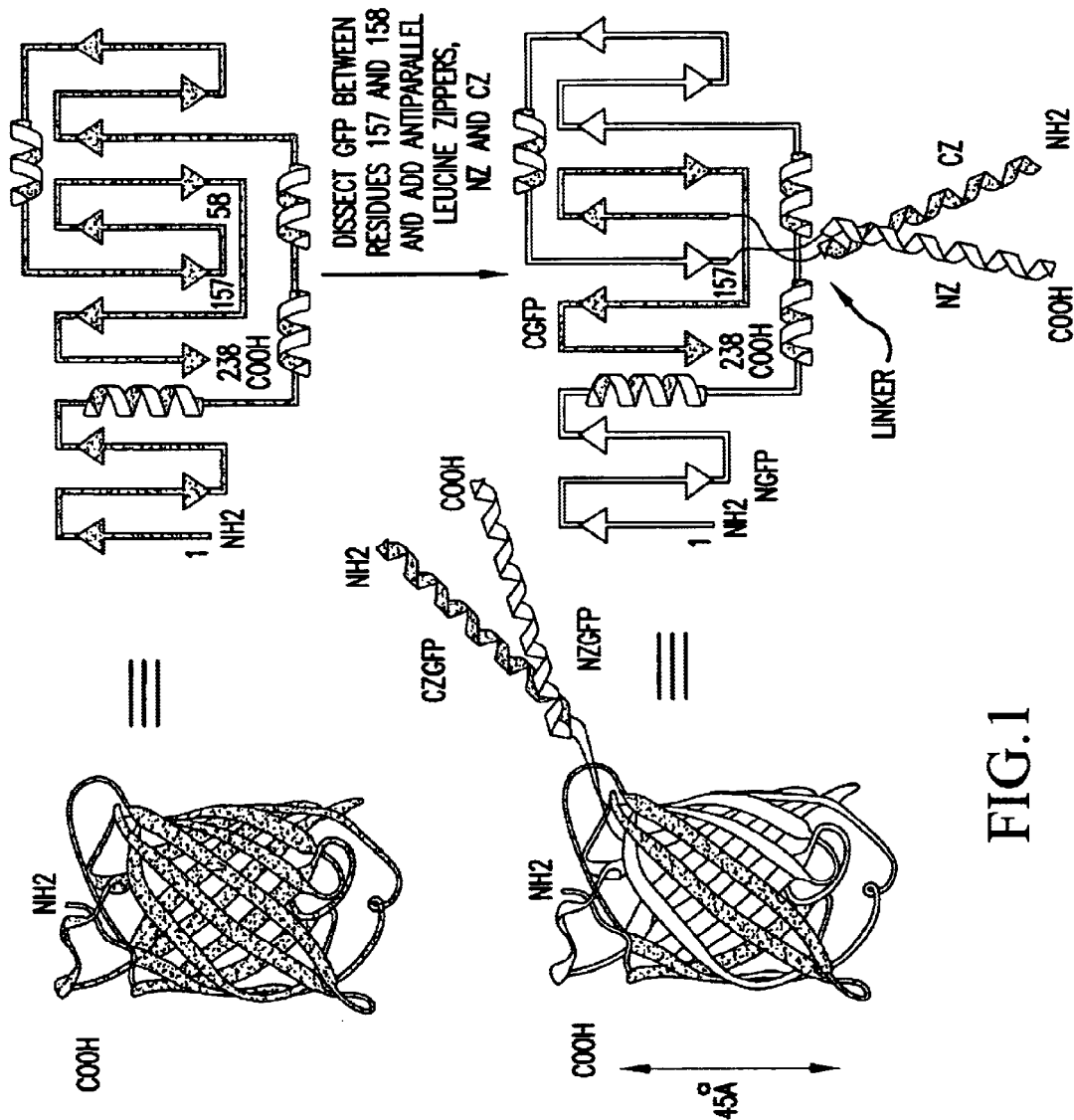
FIG. 1 shows the strategy for antiparallel leucine zipper directed protein reassembly of GFP (Kraulis, P. J., 1991, J. Appl. Crystallog., 24, 946–950). Both the ribbon and topographical structures are depicted: GFP is shown in green, NZGFP is shown in blue and CZGFP is shown in red. The sequences of the designed leucine zippers, NZ and CZ, are ALKKELQANKKELAQLKWELQALKKELAQ (SEQ ID NO: 1) and EQLEKKLQALEKKLAQLEWKNQALEKKLAQ (SEQ ID NO: 2) respectively.

The present invention is based on the finding that the dissection and subsequent reassembly of a protein from peptidic fragments provide an avenue for controlling the protein's tertiary structure and hence its function.

The present invention is based in part on the surprising discovery of a general method for the reassembly of protein fragments mediated by the non-covalent association of anti-parallel leucine zippers (Lupas, A., 1996, Trends Biochem. Sc. 21, 375–382; Kohn, W. D. et al., 1997, J. Biol. Chem. 272, 2583–2586; Bryson, J. W. et al., 1995, Science, 270, 935–941). Specifically, the present invention discloses a strategy for the noncovalent reconnection of the N- and C-termini of a dissected surface loop of a protein by means of antiparallel leucine zippers (FIG. 1) (Kraulis, P. J., 1991, J. Appl. Crystallog., 24, 946–950). The present invention demonstrates the successful application of this oligomerization strategy, both in vitro and in vivo, to the 238 residue green fluorescent protein (GFP) from Aequorea victoria (Tsien, R. Y., 1998, Annu. Rev. Biochem., 67, 509–544). GFP provides an easily testable system for correct reassembly by virtue of its autocatalytically generated fluorescence, which is intimately linked to its properly folded structure (Ormo, M. et al., 1996, Science, 273, 1392–1395; Reid, B. G. et al., 1997, Biochemistry, 36, 6786–6791; Miyawaki, A. et al., 1997, Nature, 388, 882–887; Miesenbock, G. et al., 1998, Nature, 394, 192–195;).

The present invention is also based in part on the discovery of an effective strategy involving linking fragments of an enzyme to potentially interacting protein-partners such that functional enzyme reassembly only occurs on formation of a strong protein-protein complex. In one aspect, the present invention establishes the selectivity of the GFP reassembly mediated selection of interacting proteins (GRIP) assay and applies it to the in vivo calorimetric selection of complementary leucine zipper pairs from combinatorial libraries in Escherichia coli. In another aspect, the present invention demonstrates the applicability of the GRIP assay to monitor the disruption of protein-protein interactions by a dominant negative approach. Accordingly, the present invention provides an assay system that has the potential to monitor protein-protein interactions in their natural environment within a cell and are not limited to the nucleus as are classic yeast two-hybrid systems (Fields, S. et al., 1989, Nature, 245–246).

2. Definitions

As used herein, "active protein complex" refers to a protein complex comprising two or more peptides and retaining substantially all the functional activity of the native protein from which the peptides are obtained.

As used herein, "covalent bond" refers to an interatomic bond characterized by sharing of electrons.

As used herein, "fusion protein" or "chimeric protein" refers to a hybrid protein, which consists of two or more proteins, or fragments thereof, linked together covalently. A fusion protein may comprise two or more peptides or proteins from different animals, origins, or species.

As used herein, "helical domain" refers to a protein or polypeptide fragment or a peptide having a α helix or a coiled configuration.

As used herein, "heterologous protein or peptide" refers to a protein or peptide derived from a different origin, animal, or species. Heterologous proteins or peptides are not operably linked in their naturally occurring or native form.

As used herein, "noncovalent association" refers to molecular interactions that do not involve an interatomic bond. Noncovalent interactions involve, for example, ionic bonds, hydrogen bonds, hydrophobic interactions, and van der Waals forces. Noncovalent forces may be used to hold separate polypeptide chains together in proteins or in protein complexes.

As used herein, "protein complex" refers to a combination of two or more proteins into a larger molecule without covalent bonding.

As used herein, "random peptide" refers to an oligomer composed of two or more amino acid residues and constructed by a means with which one does not preselect the complete sequence of a particular oligomer.

As used herein, "random peptide library" or a "combinatorial library" refers a library comprising not only a set of recombinant DNA vectors (also called recombinants) that encodes a set of random peptides, but also random peptides encoded by those vectors, as well as the fusion proteins containing those random peptides.

As used herein, "signaling moiety" refers to a moiety that acts to cause an action such as a signal. The moiety may signal as a result of an enzymatic reaction, light absorption, or other means.

3. Specific Embodiments

A. GFP as a System for Protein Reassembly and Fragment Complementation Assay

The present invention is based in part on the use of GFP as model for protein reassembly and fragment complementation based assays. GFP provides an ideal system for these assays because the reassembled protein autofluoresces and is easily visualized and amenable to fluorescence activated cell sorting (Tsien, R. Y., 1998, Annu. Rev. Biochem., 67, 509–544; Misteli, T. et al., 1997, Nat. Biotechnol. 15, 961–964). GFP fluorescence does not require the addition of other cellular factors, substrates, or additional gene products from A. victoria. Moreover, GFP can be expressed and detected in various cells and organisms and is not localized to a specific organelle of a cell upon expression. Additionally, unlike the DHFR assay, detection of GFP expression is not dependent upon survival or death of host cells. Nor is the expression of GFP dependent upon the addition of cofactors as in the β-galactoside assay or of other cellular components as in the ubiquitin assay. It is also not toxic to mammals and has been expressed in monkeys (Chan et al., 2001, Science, 291, 309). Further, the multiple variants of GFP available for use in different organisms and cell-types make it an ideal protein candidate for development of a general assay such as the GRIP assay described below.

Various mutations in GFP leading to brighter emission following 488 nm excitation have been generated. Mutations in GFP which shift the excitation maximum from 395 nm to about 490 nm have been reported by Delagrave et al. (1995, Biotechnology, 13, 151) and Heim et al. (1995, Nature, 373, 663). Mutants with Ala, Gly, Ile, Cys or Thr substituted for Ser65 have large shifts in excitation maxima, and fluoresce more intensely than wild-type protein when excited at 488 nm. The mutation of Ser65 to Thr or Cys has been observed to increase by a factor of 6 the fluorescence of GFP following 488 nm excitation. Heim et. al. (1994, Proc. Nat'l Acad. Sci USA, 91, 12501–12504) describe a mutant that fluoresces blue and contains a histidine in place of Tyr66. Delagrave et al. (1995, Bio. Technology, 13, 151–154) report on several Aequorea GFP variants that showed red-shifted excitation spectra, i.e., shift in excitation maxima from 393 nm to 498 nm. Delagrave et al. hypothesize that co-expression of GFP and red-shifted GFP (RSGFP) will enable the analysis of two proteins or promoters per cell or organism.

U.S. Pat. No. 6,096,865 describes GFP mutants with improved solubility properties at higher temperatures and are able to fluoresce at 37° C. Specifically, the patent provides a GFP mutant in which phenylalanine at original amino acid position 64 is replaced by a leucine. This mutant has the ability to fluoresce at 37° C. Other mutants with altered spectra are disclosed by Heim et al. (1994, Proc. Nat'l Acad. Sci USA, 91, 12501–12504 and 1995, Nature, 373, 663).

The present invention contemplates the use of various GFP mutants in the protein complementation assay and protein reassembly assay described in detail below. The preferred GFP mutant is the sg100 GFP variant described below.

B. Methods for Reassembly of Fragments into a Functional Protein

Figure 2:
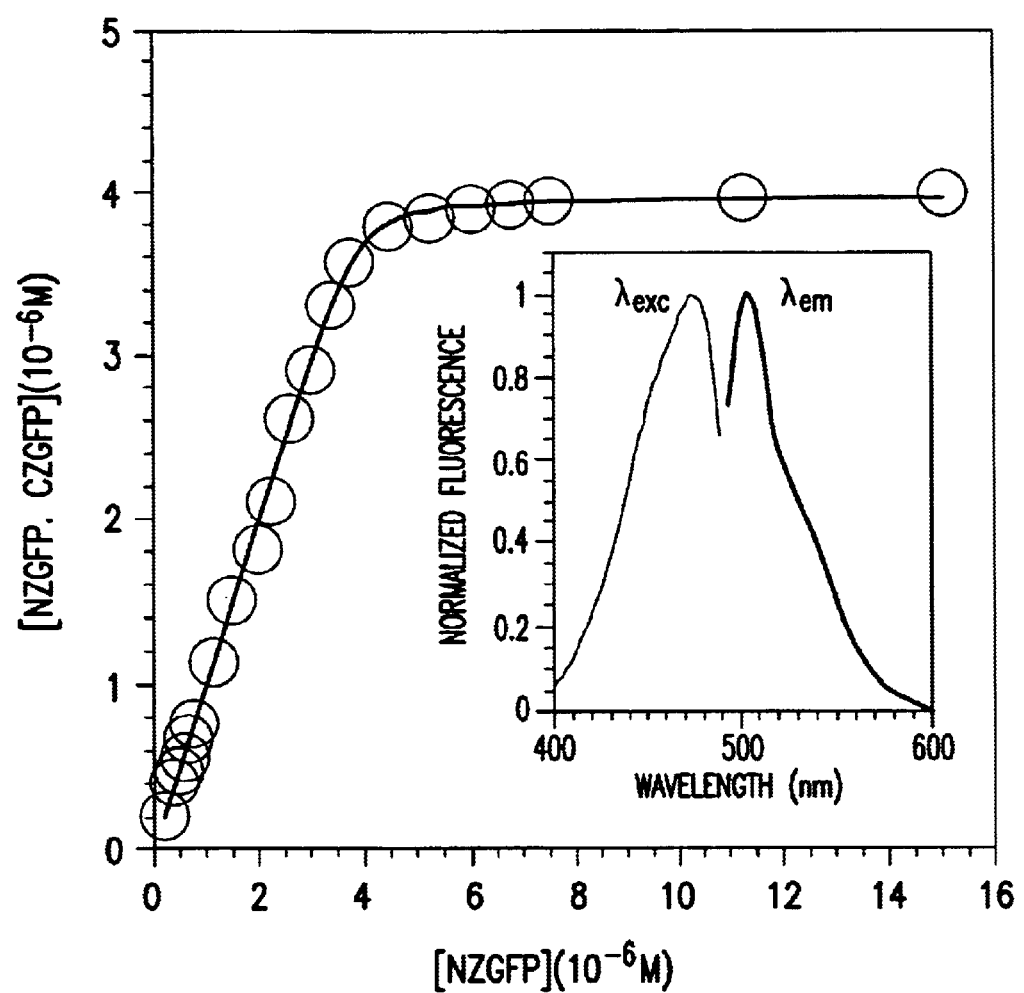
FIG. 2 shows fluorescence binding isotherm for the interaction of NZGFP with CZGFP monitored at 505 nm. Inset shows the normalized fluorescence excitation and emission of the reconstituted NZGFP.CZGFP complex.

The present invention also is based in part on the discovery that an antiparallel leucine zipper is useful for in vitro reassembly of protein fragments into a functionally active protein. Specifically, a GFP variant (sg100) which has a single excitation and emission maximum at 475 nm and 505 nm respectively, was dissected and refolded using an antiparallel leucine zipper. The GFP variant, sg100, was dissected at a surface loop between residues 157 and 158. A pair of helices, NZ and CZ (SEQ ID NO: 1 and 2), capable of forming an antiparallel leucine zipper was designed and fused to the dissected GFP fragments via linkers to form NZGFP (N-terminal GFP) and CZGFP (C-terminal). Under conditions routinely used for folding denatured GFP, NZGFP and CZGFP reassembled properly to form a functionally active GFP. The wavelengths, $\lambda_{max}$, for fluorescence excitation and emission spectra were identical to that of the parent GFP (FIG. 2).

The present invention is also based in part on the discovery that an antiparallel leucine zipper is useful for in vivo reassembly of protein fragments into a functionally active protein. Specifically, equimolar amounts of plasmids encoding NZGFP and CZGFP were transformed into E. coli cells. Colonies that turned green (FIG. 3, panel a) were selected and further cultured in liquid media for analysis of the protein expression pattern. As shown in FIG. 3, panels b and c, the green colonies expressed similar amounts of NZGFP and CZGFP, whereas the non-fluorescent colonies contained either NZGFP or CZGFP. Moreover, control cotransformation experiments with NGFP/CGFP, NGFP/CAFP, and NZFP/CGFP did not have any green colonies. Accordingly, the presence of both NZ and CZ leucine zippers are required to mediate GFP assembly in vivo and in vitro.

The present invention contemplates the use of the antiparallel leucine zipper to refold, reconstitute, or reassemble proteins from peptides. Moreover, the ability to reconstitute GFP from its peptide fragments can be extended to an in vivo fragment complementation assay for the selection of antiparallel leucine zippers as has been demonstrated for parallel leucine zippers with DHFR (Pelletier, J. N. et al., 1999, Nat. Biotechnol., 17, 683–690). As described below, fragmented GFP can be used to study the in vivo interaction of protein-protein pairs which have their N and C termini in close proximity (Pelletier, J. N. et al., 1998, Proc. Natl. Acad. Sci. U.S.A., 95, 12141–12146). More generally, the protein reassembly strategy of the present invention may have applications such as the selective isotopic labeling of one fragment of a large protein for NMR analysis, or the mutagenesis of a limited region of a protein as demonstrated for inteins (Cotton, G. J. et al., 1999, J. Am. Chem. Soc., 121, 1100–1101; Cotton, G. J. et al, 1999, Chem. Biol., 6, R247–R256; Muir, T. W. et al., 1998, Proc. Natl. Acad. Sci. U.S.A., 95, 6705–6710; Xu, R. et al., 1999, Proc. Natl. Acad. Sci. U.S.A., 96, 388–393). Further, the engineering of an on/off switch for the activity of fragmented proteins by designing a leucine zipper heterodimer which can be reversibly assembled or disassembled by controlling the environmental conditions is also contemplated (Zutshi R. et al., 1998, *Curr. Opin. Chem. Biol.*, 2, 62–66; Yao, S. et al., 1998, *Nature*, 396, 447–450; Krylov, D. et al., 1994, *EMBO J.*, 13, 2849–2861).

C. GRIP Assay and Combinatorial Selection

The present invention is also based on the selectivity of the GFP reassembly mediated selection of interaction proteins. Based on this selectivity, the present invention developed the GRIP assay (GFP reassembly mediated selection of interacting proteins or peptides) and applied the assay to the in vivo colorimetric selection of complementary leucine zipper pairs from combinatorial libraries.

Specifically, the inventors having established that the GRIP assay was selective for high affinity LZ (leucine zipper) pairs, tested the applicability of the assay in the combinatorial selection of LZ pairs that would interact strongly enough to promote GFP reassembly (FIG. 5A). This would extend the GRIP system for selection of protein partners as had been demonstrated for other fragment reassembly systems (Pelletier, J. N. et al., 1999, *Nat. Biotechnol.* 17,683–690). A simple experiment in which the acidic LZ containing N-terminal GFP fragment (EE-NGFP) was kept constant was chosen. A library of LZ partners that could either code for Glu or Lys with equal probability at the e and g "specificity" positions (FIG. 5A) was generated. This library was fused to the C-terminal GFP fragment (XX-CGFP). The plasmid encoded library of XX-CGFP and EE-NGFP were cotransformed into host cells, and colonies that exhibited fluorescence were selected and analyzed by sequencing. As expected, there was an overall enrichment of Lys residues as the selected partner for complementing the acidic EE-NGFP. The electrostatic pairing of Lys/Glu is required for stabilizing the leucine zipper.

The present invention demonstrates that the GRIP assay is selective for specific protein pairs in vivo and is amenable for the selection of complementary protein pairs in vivo.

Figure 6:
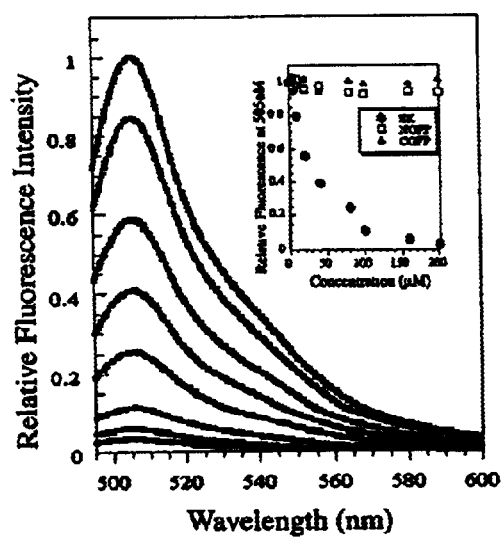
FIG. 6 shows fluorescence spectra for the dominant negative inhibition of NGFP/CGFP complex formation as a function of added EK leucine zipper inhibitor (SEQ ID NO: 1). Inset shows the inhibition profiles of the EK leucine zipper, NGFP, and CGFP peptides.

D. GRIP Assay and its Use in Detection of Inhibitors or Protein-Protein Interactions The present invention is further based in part on the discovery that the GRIP assay is useful for assaying the disruption of protein-protein interactions in vitro. The GRIP can be utilized for identifying inhibitors of protein-protein interactions. Specifically, a LZ peptide (SEQ ID NO: 1) was incubated with NGFP/CGFP complex. The sample was monitored for fluorescence as a function of added peptide (FIG. 6). The LZ peptide (SEQ ID NO: 1) prevented the assembly of the complex (4 $\mu$M) with an IC$_{50}$ value of 31 $\mu$M. Control experiments with addition of either NGFP or CGFP fragments that lacked leucine zippers did not prevent reassembly of NZGFP/CZGFP complex (FIG. 6).

E. Applications of the GRIP Assay

The present invention is based on the development of a visually detectable calorimetric system for studying the assembly and disassembly of protein partners. This system can be used for high-throughput screening, for example, screening using fluorescence activated cell sorting in yeast (Winson, M. K. et al., 2000, *Methods*, 21, 231–240 (2000).). Further, the system can be practiced using protein three-hybrid detection system, with two interacting proteins fused to respective fragments of a donor GFP variant and a third protein fused to an acceptor GFP variant, thus allowing for in vivo fluorescence resonance energy transfer measurements (Tsien, R. Y., 1998, *Annu. Rev. Biochem.*, 67, 509–544; Pollok, B. A. et al., 1999, *Trends Cell Biol.*, 9, 57–60).

In the GRIP assay, the emitted light can be analyzed by visual screening, a flow sorter (FACS), a spectrophotometer, a microtiter plate reader, a charge coupled devise (CCD) array, a fluorescence microscope, or other similar devices.

The GRIP assay may be performed in using a multiwell format. Typically, wells are arranged in two dimensional linear arrays with greater than 864 wells on a standard microtiter plate footprint. Other commonly used numbers of wells include 1536, 3456, and 9600. Well volumes typically vary from 500 nanoliters to over 200 microliters, depending on well depth and cross sectional area. Well volumes of 1, 2, 5, 10, 20, and 50 microliters are commonly used. Wells can be made in any cross sectional shape (in plan view) including, square, round, and hexagonal and combinations thereof. Wells can be made in any cross sectional shape (in vertical view), including shear vertical walls with flat or round bottoms, conical walls with flat or round bottoms and curved vertical walls with flat or round bottoms and combinations thereof.

U.S. Pat. No. 6,229,603 provides multi-well plates with greater than 864 wells that comprise a layer of cycloolefin having low fluorescence and high transmittance. These multi-well plates are particularly well suited for fluorescence measurements.

The GRIP assay may be used to study protein-small molecule interactions. Alternatively, the assay may be used to investigate protein-protein interactions and to screen libraries for identification of binding molecules. Examples of protein-protein interactions include, but are not limited to, antigen/antibody, ligand/receptor, antagonist or inhibitor/protein, binding protein/protein, and enzyme/substrate.

Further, the GRIP assay may be used to investigate other macromolecular interactions. A known DNA or RNA binding protein, "A" (that binds a RNA or DNA sequence "X"), is fused to one fragment of GFP, for example NGFP, and a second putative RNA or DNA binding protein from library "Z" is fused to, for example CGFP. In an in vivo or in vitro system the DNA or RNA component ("X-Y") that is being assayed for will have the DNA or RNA sequence "X" attached to a second DNA or RNA sequence Y whose protein target is being sought from library "Z". When binding or complexing occurs between "X" and A-NGFP and "Y" with a protein from the X-CGFP library, fluorescence will be established.

Variations upon this can be used to identify carbohydrate-protein partners or small molecule protein partners by making appropriate changes in the NGFP fused protein A (which can be chosen to bind carbohydrate or small molecule components).

This assay may also be used to investigate libraries of DNA, RNA, carbohydrates, peptides or other small molecules. In this situation "X-Y" can be a library. "X" is held constant with a known DNA, RNA, carbohydrate, or small molecule that binds a protein, "A", and "Y" can be varied as desired. The fusion proteins A-NGFP and Z-CGFP can also be held constant. "Y" is identified and is a molecule that binds Z-CGFP. Establishing fluorescence will indicate identification of a DNA, RNA, carbohydrates, or small molecules component Y that binds protein Z.

F. Combinatorial Libraries

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries are well known to persons of skill in the art. Such combinatorial chemical libraries include, but are not limited to, peptide libraries (see, e.g., U.S. Pat. No. 5,010,175, Furka, 1991, *Int. J. Pept. Prot. Res.* 37, 487) and Houghton et al., 1991, *Nature* 354, 84). Other chemistries for generating chemical diversity libraries can also be used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., 1993, *Proc. Nat. Acad. Sci. USA* 90, 6909), vinylogous polypeptides (Hagihara et al., 1992, *J. Amer. Chem. Soc.* 114, 6568), nonpeptidal peptidomimetics with β-D-glucose scaffolding (Hirschmann et al., 1992, *J. Amer. Chem. Soc.* 114, 9217), analogous organic syntheses of small compound libraries (Chen et al., 1994, *J. Amer. Chem. Soc.* 116, 2661), oligocarbamates (Cho et al., 1993, *Science* 261, 1303), and/or peptidyl phosphonates (Campbell et al., 1994, *J. Org. Chem.* 59, 658), nucleic acid libraries, peptide nucleic acid libraries (U.S. Pat. No. 5,539,083), antibody libraries (Vaughn et al., 1996, *Nature Biotechnology* 14 (3), 309 and PCT/US96/10287), carbohydrate libraries (Liang et al., 1996, *Science* 274, 1520 and U.S. Pat. No. 5,593,853), small organic molecule libraries (benzodiazepines, Baum, *C&EN January* 18, page 33 (1993); isoprenoids U.S. Pat. No. 5,569,588; thiazolidinones and metathiazanones U.S. Pat. No. 5,549,974; pyrrolidines U.S. Pat. Nos. 5,525,735 and 5,519,134; morpholino compounds, U.S. Pat. No. 5,506,337; benzodiazepines U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

The small molecules of a small molecule combinatorial library may be selected from at least one of the group consisting of amino acids, peptides, oligonucleotides, and heterocyclic compounds. The present invention contemplates combinatorial libraries of small molecules that are naturally occurring or synthetic.

Suitable peptides comprise as few as two amino acids to as many as about 30; preferably, suitable peptides comprise from about two amino acids to about fifteen; most preferably, suitable peptides comprise from about two amino acids to about ten. Any amino acid may be incorporated into peptides screened and identified using the present invention, including any combination of the naturally occurring proteinogenic amino acids as well as amino acids not naturally occurring in proteins such as, but not limited to, dextrorotatory forms of the known amino acids, for example.

Suitable oligonucleotides consist of as few as two nucleotides to as many as about 50; preferably, suitable oligonucleotides consist of from about five nucleotides to about 30; most preferably, suitable oligonucleotides consist of from about five oligonucleotides to about 15. Any nucleotide may be incorporated into an oligonucleotide to be screened and identified using the present invention, including any combination of the naturally occurring deoxyribonucleotides and ribonucleotides as well as those not naturally occurring in biological systems, such as, but not limited to, H-phosphonate derivatives, N-blocked-5'-O-DMT-deoxynucleoside 3'-(2-cyanoethyl-N,N-diisopropyl) phosphoramidites, N-blocked-5'-O-DMT-deoxynucleoside 3'-(2-cyanoethyl-N,N-diisopropyl)phosphoramidites, N-blocked-5'-O-DMT-deoxynucleoside 3'-(methyl-N,N-diisopropyl) phosphoramidites, N-blocked-5'-O-DMT-deoxynucleoside 3'-(2-chlorophenyl) phosphates, N-blocked-5'-O-DMT-deoxynucleoside 3'-(2-chlorophenyl 2-cyanoethyl) phosphate, all of which are nucleoside derivatives used in oligonucleotide synthesis.

Suitable heterocyclic compounds consist of, at minimum, a single four membered ring to as much as a multiple of four membered or greater membered rings coupled by carbon chains of 1 to about 20 atoms in length, such chains being saturated or not. Preferably, suitable heterocyclic compounds include a single four- to seven-membered ring, as well as, but not limited to varying combinations of 5, 6, or 7 membered rings having varying numbers of N, S, or O atoms. Examples of suitable heterocyclic compounds include benzodiazepine and derivatives thereof (as, for example, disclosed in Bunin et al., 1992, *J. Am. Chem. Soc.* 114, 10997), penicillins, cephalosporins, and folate derivatives.

For ease of identification, the molecules in a small molecule combinatorial library may be tagged for decoding their identity.

The GRIP assay may be used to screen mixed libraries. Mixed libraries of small molecules comprising amino acids, peptides, oligonucleotides, and heterocyclic compounds that are 5'-hydroxyl derivatives of the oligonucleotides may be used. The peptide end of members of a peptide library can be modified to include a carboxyl group. A process of esterification of the carboxyl group with the 5'-hydroxyl of the oligonucleotide is used to produce a mixed library containing peptide-oligonucleotide species. Brenner et al., (1992, *Proc. Nat'l Acad. Sci. USA* 89, 5381) also describes a method of preparation of mixed libraries having nucleotides and peptides. A mixed library comprising a heterocyclic compound and a peptide is also prepared by the reaction of suitable functional groups present on the heterocyclic compound. For instance, the carboxyl group on a heterocyclic compound is reacted with the amino group on the peptide to provide an amide linkage.

Preferably, the GRIP assay of the present invention is used to screen peptide libraries. A comprehensive review of various types of peptide libraries can be found in Gallop et al., 1994, *J. Med. Chem.* 37:1233–1251. The use of peptide libraries is well known in the art. Peptide libraries have generally been constructed by one of two approaches.

In the first approach, peptides have been chemically synthesized in vitro in several formats. For example, Fodor et al. (1991, *Science* 251, 767) describe use of complex instrumentation, photochemistry and computerized inventory control to synthesize a known array of short peptides on an individual microscopic slide. Houghten et al. (1991, *Nature*, 354, 84) describe mixtures of free hexapeptides in which the first and second residues in each peptide were individually and specifically defined. Lam et al. (1991, *Nature* 354, 82) describe a "one bead, one peptide" approach in which a solid phase split synthesis scheme produced a library of peptides in which each bead in the collection had immobilized thereon a single, random sequence of amino acid residues.

In the second approach, peptides are expressed in biological systems as either soluble fusion proteins or viral capsid fusion proteins. A number of peptide libraries have been generated using the M13 phage. M13 is a filamentous bacteriophage that has been routinely used in molecular biology laboratories for the past 20 years. M13 viral particles consist of six different capsid proteins and one copy of the viral genome, as a single-stranded circular DNA molecule. Once the M13 DNA has been introduced into a host cell such as E. coli, it is converted into double-stranded, circular DNA. The viral DNA carries a second origin of replication that is used to generate the single-stranded DNA found in the viral particles. During viral morphogenesis, there is an ordered assembly of the single-stranded DNA and the viral proteins, and the viral particles are extruded from cells in a process much like secretion. The M13 virus is neither lysogenic nor lytic like other bacteriophage (e.g., λ); cells, once infected, chronically release virus. This feature leads to high titers of virus in infected cultures, i.e., $10^{12}$ pfu/ml.

In a preferred embodiment, a GFP peptide comprising a fragment of GFP is fused to a random peptide to form a fusion polypeptide. By "fused" or "operably linked" herein is meant that the random peptide and the GFP, are linked together, in such a manner as to minimize the disruption to the stability of the GFP structure, i.e. it retains fluorescence. The GFP fusion polypeptide of the present invention can comprise further components such as linkers or fusion partners.

The peptides (and nucleic acids encoding them) are randomized, either fully randomized or they are biased in their randomization, e.g. in nucleotide/residue frequency generally or per position. As used herein "fully randomized" means that each nucleic acid and peptide consists of essentially random nucleotides and amino acids, respectively. The nucleic acids which give rise to the peptides are chemically synthesized, and thus may incorporate any nucleotide at any position. Thus, when the nucleic acids are expressed to form peptides, any amino acid residue may be incorporated at any position. The synthetic process can be designed to generate randomized nucleic acids, to allow the formation of all or most of the possible combinations over the length of the nucleic acid, thus forming a library of randomized nucleic acids.

Alternatively, the peptide library is biased. In this case, some positions within the sequence are either held constant, or are selected from a limited number of possibilities. Individual residues may be fixed in the random peptide sequence to create a structural bias. For example, proline or bulky residues such as W, R, K, L, I, V, F or Y may be inserted to restrict the conformation of the peptide. Also, the library can be biased to a particular secondary structure such as the alpha-helical structure. Examples of helix forming residues include M, A, K, L, D, E, R, Q, F, I, and V.

In a preferred embodiment, the bias is toward peptides that interact with the known classes of molecules. For example, it is known that SH-3 peptides bind to SH-3 proteins. A large number of small molecule domains are known that are suitable as starting points for the generation of biased randomized peptides. Examples of such molecules, domains, or consensus sequences include, but are not limited to SH-2 domains, SH-3 domains, pleckstrin, death domains, protease cleavage/recognition sites, enzyme inhibitors, enzyme substrates, and Traf., and leucine zipper consensus sequence.

As discussed above, a fusion partner or linker can be added to fuse the random peptides to a GFP peptide. Fusion partners or linkers can be synthetic or heterologous (not native to the host cell). Appropriate fusion partners include, but are not limited to peptides that are stability sequences that stabilize and protect the random peptide from degradation, linker sequences for decoupling the random peptide from the GFP fragment, structural sequences that restrict and stabilize the conformation of the random peptide, targeting sequences which allow localization of the peptide into a subcellular or extracellular compartment, and rescue sequences that allow the purification or isolation of the random peptide.

In light of the foregoing general discussion, the specific examples presented below are illustrative only and are not intended to limit the scope of the invention. Other generic and specific configurations will be apparent to those persons skilled in the art.

EXAMPLES

General Materials and Methods

GFP Variant. A variant of the naturally occurring GFP, which has a single excitation maximum at 475 nm was chosen for dissection and reassembly. The GFP variant (sg100) contains F64L, S65C, Q80R, Y151L, I167T and K238N mutations from wild type GFP, which leads to a single fluorescence excitation and emission maximum at 475 nm and 505 nm respectively, similar to GFP-sg25 as described by Palm, G. J et al., 1997, Nat. Struct. Biol., 4, 361–365.

Cloning and Purification Protocol for NZGFP, NGFP, CGFP, and CZGFP: The NZGFP, NGFP, CGFP and CZGFP coding DNA were obtained by PCR amplification of the GFP (sg100) plasmid template using appropriate primers. The DNA fragments were cut with NheI/BamH1 and ligated into the pET11a vector. The DNA sequences of the NZGFP, NGFP, CGFP, and CZGFP containing clones were verified by dideoxyoligonucleotide sequencing at the Keck facility at Yale. The protein products were overexpressed in BL21 (DE3) cells at 37° C. without IPTG induction. The cells were lysed by sonication and the proteins were individually purified by passage over 2 successive Q-sepharose columns and then over a Gel-filtration column. Fractions containing the protein of interest, as determined by SDS-PAGE, were pooled and dialyzed against 2 mM DTT, 10 mM TrisHCl buffer at pH 7.2. Final purified yields of proteins were between 10–20 mg/ L. Protein molecular weights were verified by MALDI mass spectrometry to within 0.05% of the calculated molecular weight. Amino acid analysis of the proteins established the correct compositions and protein concentrations for further biophysical studies.

Amino acid sequences of NGFP, NZGFP, CGFP, and CZGFP: Leucine zippers are in bold and linker regions underlined. Note the 6 residue linker between the C-terminal of NGFP and NZ and the 4 residue linker between CGFP and CZ.

```
NGFP
     MASKGEELFTGVVPILVELDGDVNGHKFSVSGEGEGDATYGKLTLKFIC         (SEQ ID NO: 3)

TTGKLPVPWPTLVTTLCYGVQCFSRYPDHMKRHDFFKSAMPEGYVQERTIFFKD

DGNYKTRAEVKFEGDTLVNRIELKGIDFLEDGNILGHKLEYNYNHNVLIMADKQ

GGSGSG

NZGFP
     MASKGELLFTGVVPILVELDGDVNGHKFSVSGEGEGDATYGKLTLKFIC         (SEQ ID NO: 4)

TTGKLPVPWPTLVTTLCYGVQCFSRYPDHMKRHDFFKSAMPEGYVQERTIFFKD

DGNYKTRAEVKFEGDTLVNRIELKGIDFKEDGNILGHKLEYNYNHNVLIMADKQ

GGSGSGALKKELQANKKELAQLKWELQALKKELAQ

CGFP
     MASGGSGKNGIKVNFKTRHNIEDGSVQLADHYQQNTPIGDGPVLLPDNH         (SEQ ID NO: 5)

YLSTQSALSKDPNEKRDHMVLLEFVTAAGITHGMDELYN

CZGFP
     MASEQLEKKLQALEKKLAQLEWKNQALEKKLAQGGSGKNGIKVNFKTRH         (SEQ ID NO: 6)

NIEDGSVQLADHYQQNTPIGDGPVLLPDNHYLSTQSALSKDPNEKRDHMVLLEF

VTAAGITHGMDELYN
```

Additional Constructs for GFP Reassembly: DNA constructs for EE-NGFP and KK-CZGFP coding DNA were obtained by PCR amplification of the GFP (sg100) plasmid template using appropriate primers encoding the leucine zippers KK and EE whose sequences are AQLKEKLQALKEKLAQK WKLNALKEKLAQ (SEQ ID NO: 7) and ALEKELQANEKELAQLEWELQALEKELAQ (SEQ ID NO: 8) respectively. The DNA fragments were digested with NheI/BamH1 (New England Biolabs) and ligated into the pET11a vector. The DNA sequences of the EE-NGFP, and KK-CGFP containing clones were verified by automated sequencing at the Keck facility at Yale.

Constructs for Library Selection: For leucine zipper library construction, two overlapping degenerate oligonucleotides containing NAG (N=G or A) at all positions corresponding to Lys in the leucine zipper of KK-CGFP were synthesized such that they would code for either Lys or Glu with equal probability. The two overlapping oligonucleotides were mutually primed and extended using T7 Sequenase (Amersham) with 10 mM dNTPs. The product was purified from an agarose gel and subsequently ligated into the NheI-DraIII (New England Biolabs) cassette present in a previously cut KK-CGFP plasmid. The resulting library, XX-CGFP, was transformed in 5×50 µL of electrocompetent XL1-Blue cells (Stratagene) and selected for ampicillin resistance. The resulting pool of XX-CGFP plasmids was sequenced to verify that G/A were equally represented at sites of randomization.

Colorometric Selection: For all reassembly experiments with NZGFP/CZGFP, NZGFP/KK-CGFP, EE-NGFP/CZGFP, and EE-NGFP/KK-CGFP: 1 µg of each plasmid was cotransformed in 30 µL of BL21 (DE3) cells and selected on ampicillin containing LB plates. The plates were incubated at 37° C. overnight and subsequently moved to the bench top (23° C.) for 2 days. The green color developed after 16–32 hours. The cotransformation efficiency was approximately 7±2% as verified by growing up individual colonies and monitoring protein expression profiles, which corresponded well with visual inspection of green colonies in experiments with NZGFP/CZGFP and EE-NGFP/KK-NGFP. Non-fluorescent colonies that coexpressed either NZGFP/KK-CGFP or EE-NGFP/CZGFP were identified by screening 120 colonies of respective cotransformations by SDS gel for protein expression of both gene products. In library selections, 20 individual cotransformations of 1 µg of XX-CGFP library plasmid with 1 µg of EE-NGFP plasmid were carried out as described above. Sixteen colonies were selected from 102 green colonies of ~4000 total colonies. The colonies were grown overnight in LD media and the plasmid DNA (XX-CGFP+EE-NGFP) purified and sequenced using primers unique to the XX-CGFP construct.

Inhibition of Protein-Protein Interactions: The protein products for NZGFP, CZGFP, NGFP and CGFP were overexpressed in BL21 (DE3) cells at 37° C. and purified as described above. Amino acid analysis of the proteins established the correct compositions and protein concentrations for fluorescence experiments. The inhibitor peptide corresponding to the leucine zipper of NZGFP (EK peptide) having the sequence ALKKELQANKKELAQLKWELQALKKELAQ (SEQ ID NO: 1) was synthesized at the Keck facility (Yale University) and purified on a reverse phase C8 column (Vydac) by HPLC. Peptide concentrations were determined by Trp absorbance and verified by amino acid analysis.

For inhibition experiments all fluorescence measurements were made in triplicate on a Hitachi F-4500 Fluorescence Spectrophotometer with excitation at 475 nm and emission at 505 nm. A 1.2 mM stock solution of equimolar amounts of NZGFP/CZGFP was allowed to reassemble and fluoresce until there was no change in fluorescence (36 hours). The reassembled complex was denatured in 4 M GdmHCl for 4 hours following which different concentrations of EK peptide, NGFP, or CGFP were added and the NZGFP/CZGFP concentration adjusted to 800 µM. The samples were diluted 200 fold into 2 mM DTT, 10 mM Tris.HCl buffer at pH 7.2 to a 20 mM final concentration of Gdm.HCl and allowed to refold and fluoresce. In order to eliminate artifacts from time dependent inhibition, fluorescence measurements were made after 4 hours and after 16 hours and found to be constant.

Example 1

In Vitro Reassembly of GFP Using an Antiparallel Leucine Zipper

1. Design of Antiparallel Leucine Zipper

Designs for helices, designated NZ and CZ, to form antiparallel leucine zippers for reassembly purposes were based upon sequences reported by Hodges, (11a) Kim, (Oshea, E. K. et al., 1993, Current Biol., 3, 658–667) and Alber (Harbury, P. B. et al., 1994, Nature, 371, 80–84). The leucine zippers contained a Leu-rich hydrophobic core, acidic (Glu) and basic (Lys) residues to direct antiparallel heterodimer formation, and also incorporated a buried asparagine residue which disfavors homodimerization by up to 2.3 Kcal/mol (FIG. 1) (Oakley M. G. et al.; 1998, Biochemistry, 37, 12603–12610).

Dissection of GFP

The variant GFP (sg100) was dissected at a surface loop between residues 157 and 158, a position that has previously been shown to accommodate a 20 residue amino acid insertion (Abedi, M. R., et al., 1998, Nucleic Acid Res., 26, 623–630). The dissection resulted in N-and C-terminal fragments, designated NGFP and CGFP, containing 157 and 81 residues, respectively (FIG. 1). The NGFP fragment contains the three residues, Ser65, Tyr66, and Gly67, that ultimately form the GFP fluorophore (Tsien, R. Y., 1998, Annu. Rev. Biochem., 67, 509–544)

3. In Vitro Reassembly of the Dissected GFP Fragments Using the Designed Helices The designed helix, NZ was appended to the C-terminal of NGFP, via a six residue linker, to generate the fusion peptide designated NZGFP. Similarly, CZ was appended to the N-terminal residue of CGFP, via a four residue linker, to generate the complementary fusion peptide, CZGFP.

It was envisioned that if NZGFP and CZGFP were competent to heterodimerize via the designed helices, either in vitro or in vivo, the reconstituted GFP protein would display its characteristic fluorescence, indicating the correct reassembly of the tertiary fold from the peptide fragments. The genes encoding the designed protein sequences NZGFP, CZGFP, NGFP, and CGFP were cloned and the resulting proteins overexpressed and purified using methods routinely practiced by the skilled artisan.

To investigate the viability of the protein reassembly strategy, a literature protocol devised for the refolding of denatured GFP was followed (Reid, B. G. et al., 1997, Biochemistry, 36, 6786–6791). Thus, equimolar amounts (4 $\mu$M) of the fragments, NZGFP and CZGFP, were denatured in 6 M GdmHCl and dialyzed into a buffer containing 2 mM DTT, 10 mM phosphate buffer at pH 7.2 over 24 hrs at 4° C. The reassembled peptides were visibly green. Moreover the $\lambda_{max}$ for the fluorescence excitation and emission spectra were identical to that of the parent GFP (FIG. 2 inset). To verify that the reassembly was indeed guided by the antiparallel leucine zippers, control experiments were done with fragments with and without the leucine zippers. It was found that solutions containing NGFP, CGFP, NGFP/CGFP, NZGFP/CGFP, or NGFP/CZGFP did not fluoresce, even at concentrations of over 100 $\mu$M. The apparent dissociation constant, $K_{dapp}$, for the NZGFP/CZGFP complex was determined by titrating NZGFP into a solution of CZGFP and monitoring the fluorescence emission intensity at 505 nm (FIG. 2). The data were fitted to a two-state binding isotherm, yielding a $K_{dapp}$ of 31±7 nM and $\alpha$-analysis of the binding data verified the expected 1:1 stoichiometry of NZGFP and CZGFP (Bagshaw, C. R.; et al., 1987, Spectrophotometry and spectrofluorimetry: A practical approach, pp 91–113).

Example 2

In Vivo Reassembly of the Dissected GFP Fragments

Figure 3A:
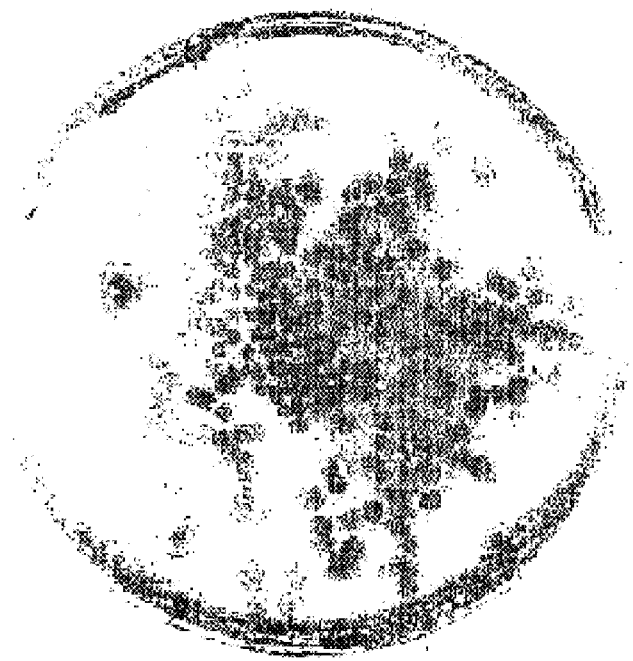
FIG. 3 shows in vitro reconstitution of GFP demonstrated by (a) green fluorescent BL21(DE3) cells and the corresponding SDS gels of (b) lane 1: MW markers; lane 2: protein from cotransformed green colony; and lane 3: protein from colony containing only NZGFP plasmid and (c) lane 1: MW markers; protein from cotransformed green colony; and lane 3: protein from colony containing only CZGFP plasmid.
Figure 3B:
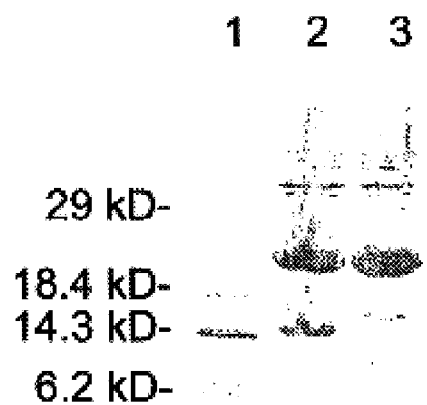
Figure 3C:
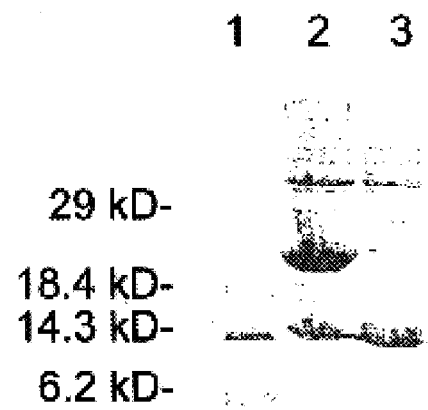
Figure 4A:
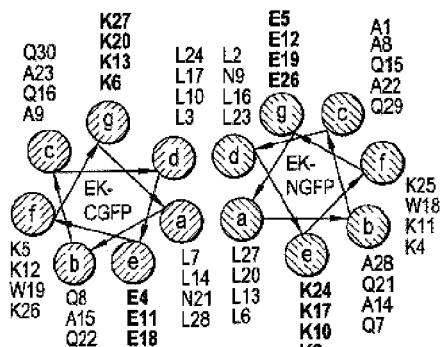
FIG. 4 shows the antiparallel leucine zipper pairs attached to CGFP and NGFP in helical wheel representations. The Lys (K) residues are colored blue and complementary Glu (E) residues are colored red. The pairs a and b are electrostatically matched and the pairs c and d are electrostatically mismatched. The inset shows restreaks of single Escherichia coil colonies corresponding to each pair. EK-CGFP is the same as CZGFP, and EK-NGFP is the same as NZGFP.
Figure 4B:
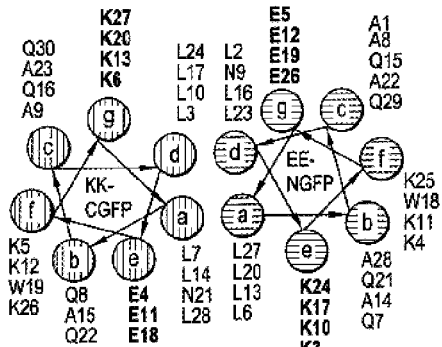
Figure 4C:
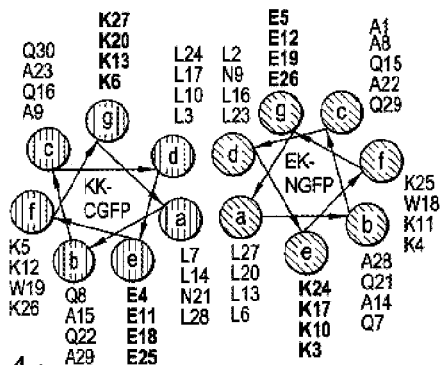
Figure 4D:
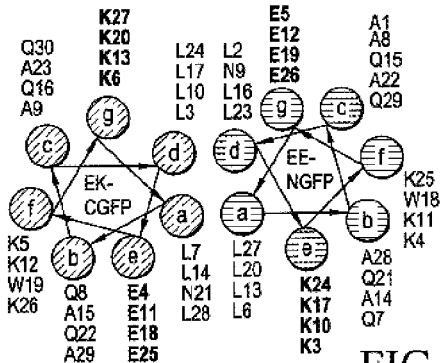

BL21(DE3) E. coli cells were transformed with equimolar amounts of NZGFP and CZGFP encoding plasmids. The appearance of green color was monitored to identify cotransformed colonies expressing reassembled GFP. After 36 hours several of the colonies turned green as illustrated in FIG. 3a. with a cotransformation efficiency of 4%. Individual colonies were cultured in liquid media and their protein expression pattern analyzed. The green colonies were shown to express similar amounts of NZGFP and CZGFP (FIG. 3b and 3c), whereas non-fluorescent colonies were shown to contain either NZGFP or CZGFP. Furthermore, control cotransformation experiments with NGFP/CGFP, NGFP/CZGFP and NZGFP/CGFP failed to show any green colonies, thus emphasizing the requirement for the presence of both NZ and CZ leucine zippers to mediate GFP assembly in vivo and in vitro.

Example 3

Reassembly of Proteins Using Antiparallel Leucine Zipper

The methods described above for reassembly of GFP in vivo and in vitro may be modified for reassembly of any protein of interest, using antiparallel leucine zippers. The particular proteins are not critical, so long as they can be divided into fragments that produce a detectable signal upon their association, specific binding, or complexation mediated by the formation of an antiparallel zipper with a known biological activity or function that can be assayed for in vitro or in vivo, for example, kinase activity for a protein kinase, proteolytic activity for a protease, and DNA binding activity of DNA binding protein.

The peptide fragments of the protein of interest are fused to each of the helices (SEQ ID NO: 1 and SEQ ID NO: 2) described above. Alternatively, other pairs of helices that form antiparallel leucine zippers may be designed and fused to the peptide fragments of the protein of interest.

1. In Vitro Reassembly

Equimolar amounts of the fusion peptides comprising peptides of the protein of interest and helices that form antiparallel leucine zippers are denatured and dialyzed as described in Example 1. The reconstitution of the protein is monitored.

2. In Vivo Reassembly

Equimolar amounts of plasmids encoding the fusion peptides are transformed in host eucaryotic or procaryotic host cells as described in Example 2. The cotransformed colonies expressing reassembled protein are identified.

Example 4

The GRIP Assay

In order to test the specificity of the GRIP assay, a set of four possible LZ combinations which were either electrostatically matched (EE-NGFP/KK-CGFP and NZGFP/CZGFP) or mismatched (EE-NGFP/CZGFP and NZGFP/KK-CGFP) (FIG. 4; Bryson, et al., 1995, Science 270, 935–941, Oakley et al., 1998, Biochemistry 37, 12603–12610) were designed. The GRIP assay would only allow the matched pairs to competently fold and catalyze fluorophore formation in GFP.

*Escherichia coli* (BL21) cells were cotransformed with plasmids encoding the proteins of interest and plated on ampicillin containing plates. Fluorescent colonies were observed only in the complementary pairs (EE-NGFP/KK-CGFP and NZGFP/CZGFP). No visible fluorescence was observed in colonies containing the uncomplementary pairs (EE-NZGFP/CZGFP and NZGFP/KK-CGFP). Since the electrostatically mismatched pairs have a dissociation constant, $K_d$, of ~100 µM (Yao, S., et al., 1998, *Nature* 396, 447–450), this experiment sets an initial lower visual limit for detecting protein-protein interactions using the GRIP assay.

Example 5

GRIP Assay and Combinatorial Selection

A library of LZ partners that could either code for Glu or Lys with equal probability at the e and g "specificity" positions (FIG. 5A) was generated (Oakley, M. G. et al., 1998, *Biochemistry* 37, 12603–12610; Pelletier, J. N. et al., 1999, *Nat. Biotechnol.* 17, 683–690; Dmitry, K., et al., 1994, *EMBO J.* 13, 2849–2861). This library was fused to the C-terminal GFP fragment (XX-CGFP). It is thought that the selected partners would be enriched in Lys in order to complement the acidic EE-NGFP.

The 256-member plasmid-encoded library of XX-CGFP was cotransformed with EE-NGFP and selected colonies that exhibited fluorescence. The protein expression profiles of the two protein fragments, XX-CGP and EE-NGFP, were virtually identical in cotransformed cells (FIG. 5B), thus excluding differences in relative protein concentration as a major determinant of the observed fluorescence. Sixteen of the multiple colonies exhibiting fluorescence were sequenced. The results of the selection are summarized in FIG. 5C. The selected LZ partners of EE-NGFP displayed an overall 3:1 ratio of Lys:Glu residues, with the fewest Lys residues being 5 and the most being 7. Thus, an overall enrichment of Lys residues was observed as predicted from the requirement for electrostatic pairing of Lys/Glu for stabilizing the leucine zipper. Assuming an average value of 0.85 kcal/mol penalty for each Glu-Glu pair relative to Lys-Glu pair based on literature precedence, (Dmitry, K., et al., 1994, *EMBO J.* 13, 2849–2861; Zhou, N. E. et al., 1994, *Protein Eng.* 7, 1365–1372), a 75 fold difference in $K_d$ between the best with all Lys ($K_d$=33 nM) (Ghosh, I. et al., 2000, *J. Am. Chem. Soc.* 122, 5658–5659) and worst (5 Lys and 3 Glu) leucine zipper partners for EE-NGFP was estimated. Thus, this experiment sets a lower threshold for the visual detection of interacting proteins in the GRIP assay to ~2.5 µM, which is within the observed dissociation constant for most specific protein partners.

Example 6

Inhibition of Protein-Protein Interactions

To verify that the GRIP assay could be utilized for detecting inhibitors of protein-protein interactions (Zutshi, R., et al., 1998, *Curr. Opin. Chem. Biol.* 2, 62–66), a LZ peptide corresponding to the LZ present in NZGFP (FIG. 4) was synthesized. The reappearance of fluorescence of the disassembled NZGFP/CZGFP complex in an in vitro assay as a function of added peptide was monitored (FIG. 6). The EK peptide (SEQ ID NO: 1) prevented the assembly of the complex (4 µM) with an $IC_{50}$ value of 31 µM. Control experiments with addition of either NGFP or CGFP fragments that lacked leucine zippers did not prevent reassembly of NZGFP/CZGFP complex (FIG. 6). It is worth noting that disassembly of an existing GFP complex was not achievable even at >1 mM added peptide inhibitor.

Example 7

GRIP Assay and Identification of Binding Partners Via Combinatorial Selection The GRIP assay may be modified by substituting the helices that form antiparallel leucine zippers with test proteins or peptides to determine whether a test protein or peptide attached to one portion of GFP interacts with another test protein or peptide attached to the other portion of GFP. The test proteins can be any protein. As an example, an orphan receptor can be fused to one portion of the GFP, while test ligands can be fused to the second portion of GFP.

Specifically, nucleic acid encoding a fusion protein comprising an orphan receptor and a first portion of the GFP and a plasmid library of fusion proteins comprising test ligands and the second portion of GFP can be cotransfected or cotransformed into host cells. Colonies exhibiting fluorescence are selected, since they contain GFP molecules that have been properly folded or reassembled, and test ligands that interact with the orphan receptor. The colonies can be further cultured and investigated to determine the structural properties of the ligand. The molecular weight of the ligand may be determined by SDS-PAGE, and the primary structure may be determined by amino acid sequencing.

Examples of orphan receptor groups include but are not limited to CCRL2, CMKLR1, CMKRL2, GPR31, HM74, and RDC 1. Specific examples of orphan receptors of each group include but are not limited to: 1) CCRL2: chemokine (C-C motif) receptor-like 2, HCR, CRAM-B, CKRX, CRAM-A, lipopolysaccharide inducible C-C chemokine receptor related, E01; 2) CMKLR1: chemokine-like receptor 1, ChemR23, CMKRL3, DEZ, CMKLR1, LOC60669: G-protein coupled chemoattractant-like receptor; 3) CMKRL2: chemokine receptor-like 2, CMKRL2, FEG-1, GPCR-BR, DRY12, CEPR, GPR30, GPR41; 4) GPR31: G protein-coupled receptor 31, GPR31, Gpr3lb; 5) HM74: putative chemokine receptor, GTP-binding protein; and 6) RDC1: chemokine orphan receptor, D2S87E, GPRN1, CMKOR1, canine orphan receptor RDC1 homolog, chemokine orphan receptor 1, Rdc1.

The GRIP assay may be modified to detect macromolecular interactions, for example, specific protein-protein interactions, both in vitro and in vivo. When the proteins attached to the two GFP fragments associate with each other, the two GFP fragments will properly reassemble and fluoresce. Thus, in the absence of association, the proteins attached to the GFP fragments do not fluoresce. Fluorescence of interacting protein pairs linked to NGFP and CGFP can provide a sensitive assay for detecting the affinity and specificity of the individual protein pairs (and their mutants) under investigation.

Examples of protein-protein interactions include, but are not limited to, antigen/antibody, ligand/receptor, antagonist or inhibitor/protein, binding protein/protein, and enzyme/substrate. Specific protein-protein interactions involved in disease and identified as potential drug targets include examples such as Bax/Bcl-2 (Sartorius, et al., 2001, *Chembiochem*, 2 (1), 20), p53/mdm2 (Moll et al., 2000, *Drug Resist. Update*, 3 (4), 217)), VEGF/VEGF-R (Plate et al., 1992, *Nature*, 359, 845), IL-6/IL-6R (Akira et al., 1993, *Adv. Immunol.*, 54, 1), Ras/Raf (Weinstein-Oppenheimer et al, 2000, *Pharmacol Ther.*, 88(3), 229).

Examples of other macromolecular interactions include, but are not limited to, nucleic acid-nucleic acid binding protein interactions and carbohydrate-protein interaction.

Example 8

GRIP Assay and Identification of Inhibitors Via Combinatorial Selection

The GRIP assay may be modified to identify inhibitors of a specific protein-protein interaction. For example, a receptor can be fused to a portion of GFP, while a ligand can be fused to a second portion of GFP. A test inhibitor, such as a test antagonist, can be incubated with the two GFP fusion proteins comprising the ligand and receptor to see if it prevents the reassembly of GFP which can be detected by the loss of fluorescence.

Specifically, nucleic acid encoding a fusion protein comprising a known receptor and a first portion of the GFP, nucleic acid encoding a fusion protein comprising its known ligand and the second portion of GFP, and a plasmid library of test antagonists can be cotransfected or cotransformed into host cells. Colonies that do not exhibit fluorescence are selected, since they contain GFP molecules that have been prevented from folding or reassembly and test antagonists that inhibit the interaction of the known receptor with its ligand. The colonies can be further cultured and investigated to determine the structural properties of the ligand. The molecular weight of the ligand may be determined by SDS-PAGE, and the primary structure may be determined by amino acid sequencing.

It should be understood that the foregoing discussion and examples merely present a detailed description of certain preferred embodiments. It therefore should be apparent to those of ordinary skill in the art that various modifications and equivalents can be made without departing from the spirit and scope of the invention. All journal articles, other references, patents, and patent applications that are identified in this patent application are incorporated by reference in their entirety.

What is claimed is:

1. A method of detecting protein-protein interaction comprising,
   (a) producing a first fusion protein and a second fusion protein, wherein:
      (1) said first fusion protein comprises
         (a) a known polypeptide linked to
         (b) a first green fluorescent protein (GFP) fragment; and
      (2) said second fusion protein comprises
         (a) a test polypeptide linked to
         (b) a second GFP fragment,
   wherein a full length GFP is dissected between the amino acid residues of a surface loop to generate said first and second GFP fragments, and wherein association of the first and second GFP fragments results in a GFP that exhibits detectable fluorescence;
   (b) detecting fluorescence from GFP, wherein said fluorescence is indicative of said test polypeptide interacting with said known polypeptide, thereby bringing said first and second GFP fragments into proximity with one another and associating to form a GFP that exhibits detectable fluorescence, which fluorescence is different from any detectable fluorescence prior to said association.

2. The method of claim 1, wherein said first and second fusion proteins are encoded by nucleic acids.

3. The method of claim 1, wherein said full length GFP is dissected between amino acid residues 157 and 158.

4. The method of claim 1, wherein the first GFP fragment is an N-terminal fragment of GFP (NGFP) and the second GFP fragment is a C-terminal fragment of GFP (CGFP).

5. The method of claim 1, wherein said first GFP fragment comprises the amino acid sequence of SEQ ID NO:3 and said second GFP fragment comprises the amino acid sequence of SEQ ID NO:5.

* * * * *